United States Patent
Zeng et al.

(10) Patent No.: US 10,952,618 B2
(45) Date of Patent: Mar. 23, 2021

(54) OPTICAL OBSERVATION EQUIPMENT AND ENDOSCOPE FOR IDENTIFYING FORMING PROCESS OF MALIGNANT TUMOR

(71) Applicants: Kun Zeng, Shanghai (CN); Guozheng Yan, Shanghai (CN); Zhenfen Yu, Shanghai (CN)

(72) Inventors: Kun Zeng, Shanghai (CN); Guozheng Yan, Shanghai (CN); Zhenfen Yu, Shanghai (CN); Wen Liu, Shanghai (CN); Xiuzhang Wang, Shanghai (CN); Zhiwu Wang, Shanghai (CN); Dasheng Liu, Shanghai (CN); Pingping Jiang, Shanghai (CN)

(73) Assignees: Kun Zeng, Shanghai (CN); Guozheng Yan, Shanghai (CN); Zhenfen Yu, Shanghai (CN)

( * ) Notice: Subject to any disclaimer, the term of this patent is extended or adjusted under 35 U.S.C. 154(b) by 1054 days.

(21) Appl. No.: 15/312,476

(22) PCT Filed: May 14, 2015

(86) PCT No.: PCT/CN2015/078924
§ 371 (c)(1),
(2) Date: Nov. 18, 2016

(87) PCT Pub. No.: WO2015/176622
PCT Pub. Date: Nov. 26, 2015

(65) Prior Publication Data
US 2017/0071472 A1     Mar. 16, 2017

(30) Foreign Application Priority Data
May 20, 2014 (CN) .......................... 201410217638.0

(51) Int. Cl.
*A61B 5/00* (2006.01)
*G16H 30/20* (2018.01)
(Continued)

(52) U.S. Cl.
CPC ........ *A61B 5/0071* (2013.01); *A61B 1/00165* (2013.01); *A61B 1/04* (2013.01);
(Continued)

(58) Field of Classification Search
CPC ... A61B 1/00131; A61B 1/00165; A61B 1/04; A61B 2576/00; A61B 5/0071;
(Continued)

(56) References Cited

U.S. PATENT DOCUMENTS 5,456,260 A * 10/1995 Kollias ............... A61B 5/0071
                                                              600/477
5,697,373 A * 12/1997 Richards-Kortum ........................
                                                      A61B 5/0071
                                                              356/301

(Continued)

FOREIGN PATENT DOCUMENTS

| CN | 1164989 | 11/1997 |
|---|---|---|
| CN | 1493250 | 5/2004 |

(Continued)

OTHER PUBLICATIONS

International Search Report, issued in the International application No. PCT/CN2015/078924, dated Aug. 5, 2015 (7 pages).

*Primary Examiner* — Amelie R Davis
(74) *Attorney, Agent, or Firm* — Hamre, Schumann, Mueller & Larson, P.C.

(57) ABSTRACT

Disclosed is optical observation equipment for identifying the forming process of a malignant tumor, which is provided with a receiving space and a transparent front end. The optical observation equipment comprises: a light-guide
(Continued)

fiber, a laser emitter, a focusing device, a white light emitter, an image sensor, a high gain amplifier and an encoding and emitting device, wherein the light-guide fiber extends to the transparent front end from the receiving space; the laser emitter emits laser with a wavelength of 340 nm±20 nm and an energy of 0.3~0.5 mj/m$^2$ in a pulsing mode; the focusing device is coupled to the output end of the laser emitter and used for focusing the laser to the input end of the light-guide fiber; the white light emitter is used for emitting white light, and the white light is guided into the input end of the light-guide fiber, wherein the laser emitter and the white light emitter are alternately turned on; the image sensor is used for acquiring an image of an area irradiated by light emitted from the output end of the light-guide fiber and converting a light signal into an electric signal; the high gain amplifier is coupled to the image sensor and is used for amplifying the electric signal generated by the image sensor; and the encoding and emitting device is coupled to the high gain amplifier and is used for encoding the signal output by the high gain amplifier and emitting the encoded signal.

8 Claims, 6 Drawing Sheets

(51) Int. Cl.
*A61B 1/00* (2006.01)
*A61B 1/04* (2006.01)

(52) U.S. Cl.
CPC .......... *A61B 5/4842* (2013.01); *A61B 5/6852* (2013.01); *A61B 5/7275* (2013.01); *A61B 5/7282* (2013.01); *G16H 30/20* (2018.01); *A61B 1/00131* (2013.01); *A61B 5/742* (2013.01); *A61B 2576/00* (2013.01)

(58) Field of Classification Search
CPC ... A61B 5/4842; A61B 5/6852; A61B 5/7275; A61B 5/7282; A61B 5/742; G16H 30/20
See application file for complete search history.

(56) References Cited

U.S. PATENT DOCUMENTS

| | | | | |
|---|---|---|---|---|
| 9,123,614 | B2* | 9/2015 | Graff | H01L 27/14683 |
| 2002/0013512 | A1* | 1/2002 | Sendai | A61B 5/0071 |
| | | | | 600/160 |
| 2003/0176768 | A1* | 9/2003 | Gono | A61B 1/0638 |
| | | | | 600/109 |
| 2008/0161699 | A1* | 7/2008 | Zeng | A61B 5/0071 |
| | | | | 600/478 |
| 2010/0249607 | A1* | 9/2010 | Yu | A61B 5/0071 |
| | | | | 600/476 |
| 2012/0016230 | A1* | 1/2012 | Kishima | A61B 1/00186 |
| | | | | 600/425 |
| 2012/0182754 | A1 | 7/2012 | Wolter | |
| 2013/0079645 | A1* | 3/2013 | Amirana | A61B 90/35 |
| | | | | 600/479 |
| 2015/0297086 | A1* | 10/2015 | Hong | G01N 21/6428 |
| | | | | 600/431 |
| 2016/0040854 | A1* | 2/2016 | Zhang | H01L 25/0753 |
| | | | | 362/242 |

FOREIGN PATENT DOCUMENTS

| | | |
|---|---|---|
| CN | 103705200 | 4/2014 |
| CN | 103989459 | 8/2014 |
| EP | 1568333 | 8/2005 |

\* cited by examiner

US 10,952,618 B2

OPTICAL OBSERVATION EQUIPMENT AND ENDOSCOPE FOR IDENTIFYING FORMING PROCESS OF MALIGNANT TUMOR

TECHNICAL FIELD

The present invention relates to the field of medical devices, more particularly relates to equipment for identifying tissues using fluorescence excited by laser irradiation.

TECHNICAL BACKGROUND

Tumors, especially malignant tumors have becoming the greatest enemy of human health. Reducing "morbidity and mortality of malignant tumor" is universally recognized as the problem for tumor. To solve this problem, scientific guidance and correct strategies are needed. "Early detection, early diagnosis and early treatment of malignant tumors" is a scientific and correct strategy. The intention of the strategy is to actively protect and control malignant tumors, rather than passively treat the malignant tumors after they are formed. Once malignant tumors are formed, it is difficult to reverse and progress quickly, meanwhile during the treatment of a tumor after the malignant tumor is formed, a large number of normal healthy cells are also killed, which significantly reduces the success of treatment and the quality of patient's life. Therefore the efficacy of passive treatment after the formation of malignant tumor is very limited, which is difficult to achieve desired results.

One of the main reasons of the high incidence of cancer in the world is that diagnostic medicine still remains in the stage of morphological diagnosis method. Morphological diagnosis methods mainly depend on the experience of physicians. Although various equipments in modern technology are used, such as endoscope, confocal laser scanning endoscope (CLE), X ray, molybdenum target, ultrasonic imaging (type-B ultrasonic), CT, and nuclear magnetic resonance (MRI), the function of these equipments is only to obtain an image. Morphological diagnosis methods are used in the process of diagnosis according to the image, and the diagnosis is based on the physician's own clinical experience. After observing the video or image provided by the above diagnostic instruments, diagnosis is made according to the morphology of image, such as bulge shape, and sunken shape, irregular particles, and island mucosa. For the formed malignant tumor, its morphological characteristics are obvious. However, at the early stage of tumor, especially when the locus of malignant tumor is smaller than 5 mm, the morphological characteristics are not obvious, and some tumors even look the same as a normal, healthy tissue. In this case, diagnosis and identification can not be morphologically carried out only relying on the physician's experience, even if a clear image is obtained by the above instruments. Therapeutically, when the locus of malignant tumor is smaller than 5 mm, it belongs to micro invasive malignant tumors or is in the stage of precancerous lesion, and if timely treated, the cure rate and survival rate of malignant tumors will be significantly improved. One-third of them can be reversed through intervention, one-third of them can be cured and recovered, and one-third of them can be treated thereby prolonging life of patients.

At present, the main direction of the development of diagnostic instruments for malignant tumor, is to continuously improve the level of imaging, but the principle and basis for diagnosis is still morphological principle. After obtaining high-resolution images, physician's experience is still needed to make a judgment. According to the above analysis, such instruments can indeed improve the diagnosis rate of malignant tumors after middle stage, and the lifecycle of patients with malignant tumor can be extended to some extent. However, after the mid-term, it is difficult to reverse and cure the malignant tumor, therefore the target of reducing "the morbidity and mortality of malignant tumor" can not be effectively achieved by these instruments.

Taking the most widely used endoscope as an example, the endoscope is widely used in diagnosis since it can enter the human body and does not cause great damage. The endoscope is developed and applied for almost half a century, and the technology is very mature and still in the process of development. Magnifying endoscopy, and ultrasonic endoscope have been developed so far, and the latest technology is confocal laser scanning endoscope (CLE). The most advanced confocal microscopy technology and sectional slices technology are used in the confocal laser scanning endoscope (CLE). An image of quasi-cellular level can be obtained (The image is a black-and-white image with unclear gradation, therefore, it can not be deemed as cellular level, but only quasi-cellular level). Confocal laser scanning endoscope (CLE) can improve the imaging level of endoscope to a new standard, and theoretically, it should greatly improve the efficiency of tumor diagnosis, however, it is not the case in actual application. Even with the help of confocal laser scanning endoscope (CLE), doctors still can not detect malignant tumors smaller than 5 mm. The reason is that confocal laser scanning endoscope (CLE) only provides images, and the final judgments are still made by the doctors based on the morphological principle and their own experience. In addition, the imaging area of confocal laser scanning endoscope (CLE) is small when providing a higher-resolution image, due to the imaging capability of confocal laser scanning endoscope (CLE) at quasi-cellular level. This requires doctors to accurately select detecting points, and the selection of detecting points is also empirically made by a doctor based on some images of lower resolution, which, theoretically, is still results from morphological judgment. Therefore, tumors in the stage of precancerous lesion, especially the malignant tumors smaller than 5 mm, cannot be effectively detected only by the method of improving image resolution, since current diagnostic methods mainly remain at the morphological level.

SUMMARY OF INVENTION

The purpose of the present invention is to provide an equipment and method for identifying tumors in the stage of precancerous lesion, especially malignant tumors smaller than 5 mm.

According to one embodiment, the present invention provides an optical observation equipment for identifying the forming process of a malignant tumor, and the optical observation equipment has a receiving space and a transparent front end, which comprises:

a light-guide fiber, the input end of which extends to the receiving space and the output end of which extends to the transparent front end;

a laser emitter, which is disposed in the receiving space and emits laser with a wavelength of 340 nm±20 nm and an energy of 0.3~0.5 mj/m$^2$ in a pulsing mode;

a focusing device, which is disposed in the receiving space and coupled to the output end of the laser emitter, and which is used for focusing the laser to the input end of the light-guide fiber;

a white light emitter, which is disposed in the receiving space and emits white light, and the white light is guided into the input end of the light-guide fiber, wherein the laser emitter and the white light emitter are alternately turned on;

a image sensor, which is disposed in the transparent front end, and which is used for acquiring an image of an area irradiated by light emitted from the output end of the light-guide fiber and converting a light signal into an electric signal;

a high-gain amplifier, which is coupled to the image sensor and is used for amplifying the electric signal generated by the image sensor;

and a encoding and emitting device, which is coupled to the high-gain amplifier and is used for encoding the output of the high gain amplifier and emitting the encoded signal.

In one embodiment, the encoded signal emitted by the encoding and emitting device is received and decoded by a receiving and decoding device, and then provided to an image processing device which restores the image acquired by the image sensor and displays the image.

In one embodiment, the laser emitter has a rated output energy >10 mj, a output pulse width <5 ns, a single pulse power >100 KW, and a repeat frequency of 1~50 times/s.

In one embodiment, the white light emitter is one or several LED(s), and the LED is aligned with the input end of the light-guide fiber. The spectrum of LED is solar spectrum with a color temperature of 5000K±400K.

In one embodiment, the light-guide fiber is quartz light-guide fiber or liquid light-guide fiber which is suitable for the transmission of ultraviolet band and visible band.

In one embodiment, the light-guide fiber shows low decay rate within the wavelength range from 300 nm to 700 nm.

In one embodiment, a graphene photosensitive element is used in the image sensor, which can perceive the fluorescence with an intensity of 0.2 lux~0.6 lux.

According to one embodiment, the present invention provides a method for identifying the forming process of a malignant tumor by using the above mentioned optical observation equipment comprising:

aligning the transparent front end of the optical observation equipment with tissue to be detected;

turning off the laser emitter, turning on the white light emitter, and irradiating the tissue to be detected with the white light emitted from the output end of the light-guide fiber;

displaying the image of the tissue to be detected which is irradiated by the white light in a display via the image sensor, the high-gain amplifier, the encoding and emitting device, the receiving and decoding device and the image processing device, and identifying suspected tissue area;

turning off the white light emitter, turning on the laser emitter, and irradiating the suspected tissue area with the laser emitted from the output end of the light-guide fiberin a pulse mode;

displaying the fluorescence image of the suspected tissue area which is irradiated by the laser in the display via the image sensor, the high-gain amplifier, the encoding and emitting device, the receiving and decoding device and the image processing device;

identifying whether or not the suspected area is relevant to malignant tumor on the basis of fluorescence color, wherein the peak value of energy at 460 nm±20 nm of normal tissue is used as a reference, if the peak value at 460 nm±20 nm is 100% of the reference value, there is no other peak values, and the fluorescence color is blue and white, the tissue is identified as normal tissue;

if the peak value at 460 nm±20 nm is more than 60% of the reference value, there is no other peak values, and the fluorescence color is orange or orange red, the tissue is identified as benign lesion tissue;

if the peak value at 460 nm±20 nm is less than 40% of the reference value, and there are peak values at 400 nm±20 nm and 670 nm±20 nm, and the fluorescence color is violet red, the tissue is identified as malignant tumor tissue;

if the peak value at 460 nm±20 nm is less than 40% of the reference value, there is peak value at 400 nm±20 nm, and the fluorescence color is violet, the tissue is identified as severe atypical hyperplasia tissue;

if the peak value at 460 nm±20 nm is less than 40% of the reference value, and there is peak value at 670 nm±20 nm, and the fluorescence color is dark red, the tissue is identified as severe atypical hyperplasia tissue;

and if the peak value at 460 nm±20 nm is less than 40% of the reference value, there is no other peak values, and the fluorescence color is dark color, the tissue is identified as mild or moderate atypical hyperplasia tissue.

According to one embodiment, the present invention provides an endoscope for identifying the forming process of a malignant tumor, and in the front end of endoscope, there is the above mentioned optical observation equipment.

In one embodiment, in the endoscope, there is also a image processing terminal which comprises a receiving and decoding device, an image processing device and a display; the encoded signal emitted by the encoding and emitting device is received and decoded by the receiving and decoding device, and then provided to the image processing device which restores the image acquired by the image sensor and displays the image by the display.

According to one embodiment, the present invention provides a method for identifying the forming process of a malignant tumor by using the above mentioned endoscope, comprising:

stretching the endoscope into a human body, and letting the front end of endoscope reach the position of tissue to be detected;

turning off the laser emitter, turning on the white light emitter, and irradiating the tissue to be detected with the white light emitted from the output end of the light-guide fiber;

displaying the image of the tissue to be detected which is irradiated by the white light in a display via the image sensor, the high-gain amplifier, the encoding and emitting device, the receiving and decoding device and the image processing device, and identifying suspected tissue area;

turning off the white light emitter, turning on the laser emitter, and irradiating the suspected tissue area with the laser emitted from the output end of the light-guide fiber in a pulse mode;

displaying the fluorescence image of the suspected tissue area which is irradiated by the laser in the display via the image sensor, the high-gain amplifier, the encoding and emitting device, the receiving and decoding device and the image processing device;

identifying whether or not the suspected area is relevant to malignant tumor on the basis of fluorescence color, wherein the peak value of energy at 460 nm±20 nm of normal tissue is used as a reference, if the peak value at 460 nm±20 nm is 100% of the reference value, there is no other peak values, and the fluorescence color is blue and white, the tissue is identified as normal tissue;

if the peak value at 460 nm±20 nm is more than 60% of the reference value, there is no other peak values, and the fluorescence color is orange or orange red, the tissue is identified as benign lesion tissue;

if the peak value at 460 nm±20 nm is less than 40% of the reference value, there are peak values at 400 nm±20 nm and 670 nm±20 nm, and the fluorescence color is violet red, the tissue is identified as malignant tumor tissue;

if the peak value at 460 nm±20 nm is less than 40% of the reference value, there is peak value at 400 nm±20 nm, and the fluorescence color is violet, the tissue is identified as severe atypical hyperplasia tissue;

if the peak value at 460 nm±20 nm is less than 40% of the reference value, there is peak value at 670 nm±20 nm, and the fluorescence color is dark red, the tissue is identified as severe atypical hyperplasia tissue;

if the peak value at 460 nm±20 nm is less than 40% of the reference value, there is no other peak values, and the fluorescence color is dark color, the tissue is identified as mild or moderate atypical hyperplasia tissue.

The optical observation equipment, the endoscope using the optical observation equipment and the related identification method of the present invention can identify the tumors the in stage of precancerous lesion, especially the malignant tumors smaller than 5 mm in time.

DESCRIPTION OF DRAWINGS

The above mentioned and other characteristics, properties and advantages of the present invention will become more obvious through the following description in combination with the drawings and examples. The same reference sign in the drawings always represents same features, wherein.

EMBODIMENTS FOR CARRYING OUT THE PRESENT INVENTION

Human tumors are generally divided into two categories, i.e., benign tumors and malignant tumors. According to the pathological classification, all of malignant tumors are derived from four kinds of tissues, i.e., epithelial tissue, mesenchymal tissue, lymphoid hematopoietic tissue, and neural tissue. Malignant tumors derived from epithelial tissue are collectively referred to as cancer. Cancer is developed inside epithelial layer. The thickness of epithelium tissue greatly varies in different organs, which is about 0.6 mm to 1.6 mm. However, the common point between them is that the lesions in early stage, which are also called precancerous lesions, occur in the thin epithelial tissue. The precancerous lesions are atypical hyperplasia according to the pathological classification. The atypical hyperplasia can be divided into three levels. The lesions are reserved within the epithelial layer, the scientific name of which is "intraepithelial neoplasia". If this kinds of tumors can be detected timely in the stage of precancerous lesion, there is great promise for curing them. As mentioned above, the stage of precancerous lesion, during which lesions are smaller than 5 mm, is the best period to diagnose and treat malignant tumors. The purpose of the present invention is to dramatically improve the detection rate of malignant tumors in the stage of precancerous lesion.

Figure 1A:
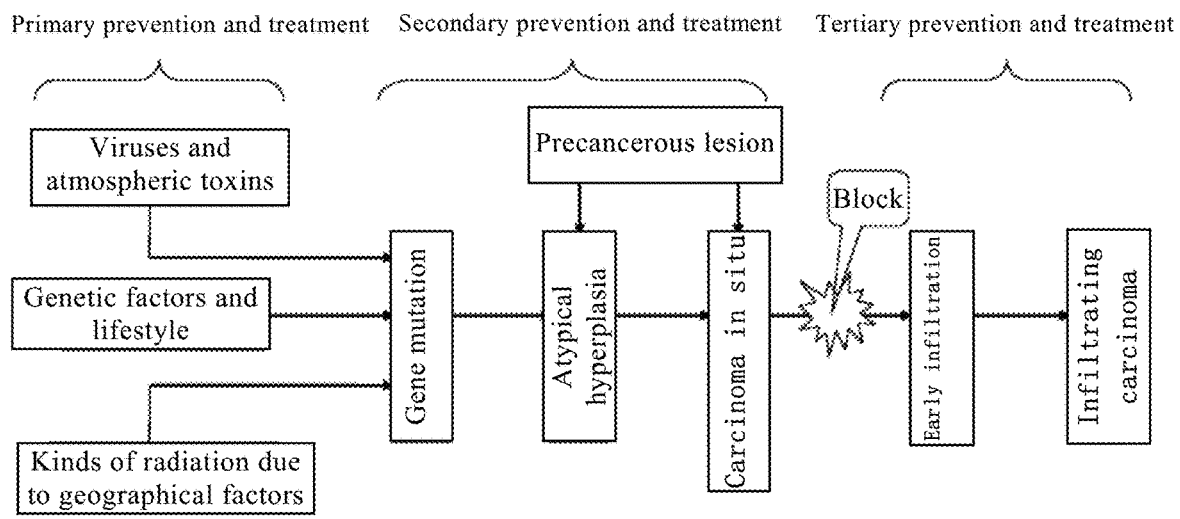
FIG. 1A shows a schematic diagram of the concept about preventing and treating malignant tumor (cancer).

FIG. 1A shows a schematic diagram of the concept about preventing and treating malignant tumor (cancer). As shown in the figure, the prevention and treatment of malignant tumor (cancer) can be divided into three stages, which is also known as prevention and treatment of three levels:

Primary prevention and treatment refers to the prevention mainly aimed at external environment, including cleaning and reducing viruses and atmospheric toxins, modifying lifestyle, investigating genetic factors, and reducing all kinds of radiation due to geographical factors. Such primary prevention and treatment mainly aims at induction factors causing gene mutation. The primary prevention and treatment involves so many factors, and not all of the induction factors will cause gene mutation, so the primary prevention and treatment currently still is a concept.

Secondary prevention and treatment refers to the detection of precancerous lesion stage. As shown in FIG. 1A, there is an atypical hyperplasia stage and a carcinoma in situ stage after gene mutation, and both of the two stages are precancerous lesion stage. "Infiltrating carcinoma" is not yet formed at these stages, and there is an incubation period for up to 5~6 years. These stages are the best time for treating malignant tumor and also the time period to which the identification method of the present invention aims. As shown in FIG. 1A, if timely and effective block can be carried on before carcinoma in situ evolves into early invasion, it will be a perfect time for the prevention and treatment of cancer.

Tertiary prevention and treatment refers to the treatment of "cancer". When entering the period of tertiary prevention and treatment, cancer has emerged which is early infiltrating carcinoma or infiltrating carcinoma. The treatment at this stage is currently used various means. But, in fact, after entering this stage cancer has been in an irreversible state.

85% of human malignant tumors derive from epithelial tissue. Of course, human malignant tumors also derive from mesenchymal tissue, lymphoid hematopoietic tissue, and neural tissue. No matter what kind of tissue a malignant tumor derives from, a long gradual process is necessary for the malignant transformation of cells. This process is known as precancerous lesion or atypical hyperplasia stage, which is also referred to the latency of malignant tumor, and the incubation period of which is usually 5~6 years. Patients in the stage of atypical hyperplasia are not malignant tumor patients in the normal sense. Atypical hyperplasia and carcinoma in situ are pathologically known as abnormal hyperplasia. Because most of lesions of abnormal hyperplasia are heteromorphic cells and a small amount of cancer cells, such abnormal hyperplasia are more likely to malignant transformation. The formation of malignant cells was not an isolated event, which needs special living environment and living condition. Malignant cells are unlikely to generate without a host providing the special environment and condition. In addition, from the perspective of molecular biology, several steps are necessary for the transformation of malignant cells from normal cells. In such process, the biochemistry environment around the cell has substantially changed, such as gene mutation, which leads to abnormal gene expression. While changes of protein and enzyme in cells would inevitably lead to various changes in metabolism, such as metabolism of porphyrin metabolism, including growth factors and hormones generated by host as well as distribution and combination of vascular for the rapid growth of malignant cells. When these prerequisites have been formed, malignant cells have conditions to survive.

Figure 1B:
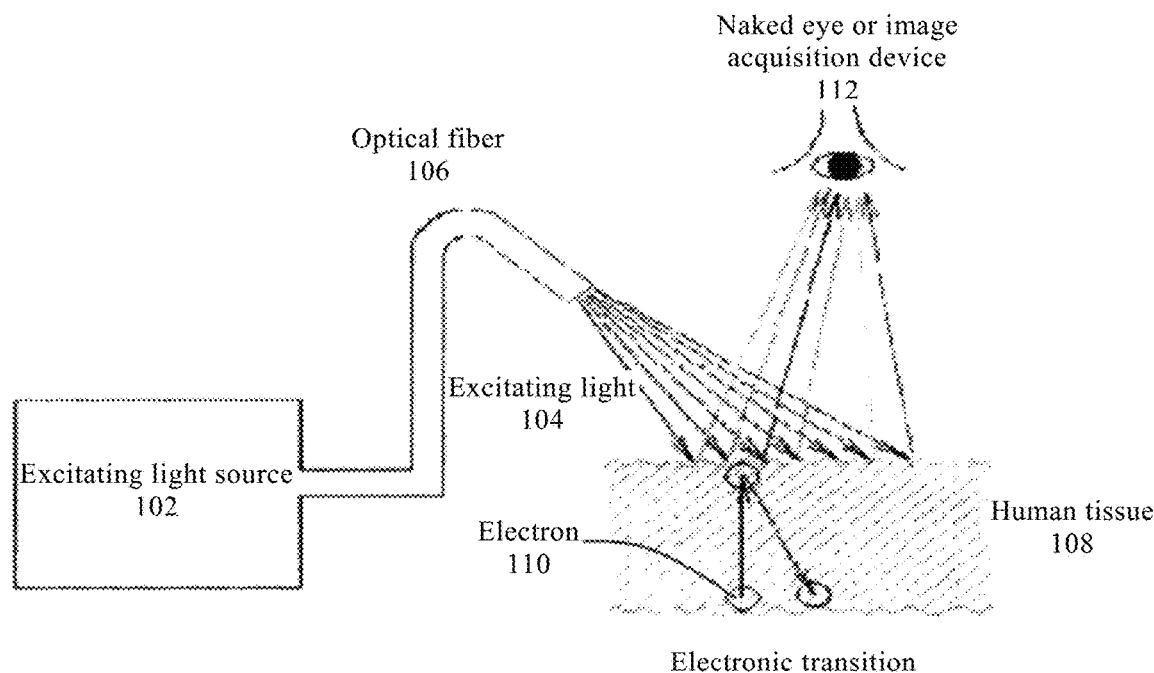
FIG. 1B shows a schematic diagram of detecting human tissue (mainly epithelial tissue or mucosa) with excitation light.

Biology research on the level of electron is quantum biology, which uses quantum mechanics as a tool in the research of biology, i.e., research in sub-molecular biology on the level of electron. Due to the advances in molecular biology and quantum biology, understanding of humans themselves has been greatly improved. The human body is made up of many molecules, mostly of which are protein macromolecules. Of course, all of biological reactions can be regarded as molecular reactions. However, the applicant believes that these reactions should not be merely reactions of macromolecules, but some smaller, more reactive and more sensitive units should participate. These units can only be non-localized electrons with high reactivity. Such single electron is prone to be motivated and strongly absorb photons, thereby exhibiting a strong color. A molecule with such unpaired electron is known as free radical, which is highly reactive (also known as electronic non-locality), therefore such molecule may produce rapid interaction with important biological significance. Except the π electron of a conjugated double bond has mobility, there are many possibilities for generation of non-locality of electrons. The color shown by fluorescence in visible light band also results from the interaction between electrons and photons. When a photon enters a substance, two cases may occur: one is that the energy is hardly absorbed after entering the substance, another is that all or part of the energy is absorbed. In the latter case, the energy of the light is transferred to molecule during the absorption process. However, the absorption itself is a highly specific phenomenon, that is, a molecular with a certain structure can only absorb a light radiation with a certain energy. As long as the energy of excitation light is strong enough, the excited molecule can obtain higher energy and transition to higher energy state. Then the molecule will transfer part of the energy to surrounding molecules through internal conversion process and return to the lowest excited state. If it does not consume energy through internal conversion and return to ground state, but releases energy by emitting corresponding photons, that is fluorescence emission. The molecular structure and surrounding environment of various species (including the biochemical environment of malignant tumor) are different. They all exhibit their own particular spectral frequency when a light of particular frequency irradiating the material (including human tissues). FIG. 1B shows a schematic diagram of detecting human tissue (mainly epithelial tissue or mucosa) with excitation light source. Wherein, an excitation light 104 emitted by a excitation light source 102 irradiate human tissue 108 (mainly epithelial tissue or mucosa) through an optical fiber 106. Electronic transition is occurred within the human tissue 108. Fluorescence is produced during the transition process of electron 110 and acquired by naked eyes or an image acquisition device 112. It can be known according to the above fluorescence mechanism, the generation of fluorescence is resulted from the change of quantum states within the molecular structure. Different molecular structures can produce different fluorescence wavelengths. At present, the basic biochemical environment surrounding a malignant tumor remains unknown, however, if there is an external exciting light with enough energy to excite malignant tumor and normal tissue, the malignant tumor and normal tissue will absorb corresponding photons which can be absorbed by them, respectively, and then return to the ground state by releasing the energy of the absorbed photons in the form of fluorescence. This released fluorescence spectrum contains a great deal of surrounding biochemical information of malignant tumor and normal tissue. The diagnostic criteria for identifying the fluorescence spectrum and fluorescence image of malignant tumor, atypical hyperplasia and benign lesion can be established with the aid of the acquired fluorescence information.

The distribution of fluorescence spectrum directly reflects the change in the energy distribution of different excited states inside a molecular structure. The optical properties of the molecule are determined by the electronic structure in a molecular, which represent the basic independent structure of each molecule. The inherent fluorescence spectrum can display characteristics of one molecular. Similarly, when a human tissue is detected using the inherent fluorescence spectrum technology, the molecular characteristics of the human tissue can also be definitely displayed. If the detected human tissue is malignant tumor tissue, atypical hyperplasia tissue, inflammatory, ulcers or normal tissue, the characteristic curve of inherent fluorescence spectrum and color image of inherent fluorescence spectrum corresponding to their own characteristics will be displayed. FIGS. 2A~2F reveal the characteristic curves of inherent fluorescence spectrum and color images of inherent fluorescence spectrum of different human tissues.

Figure 2A:
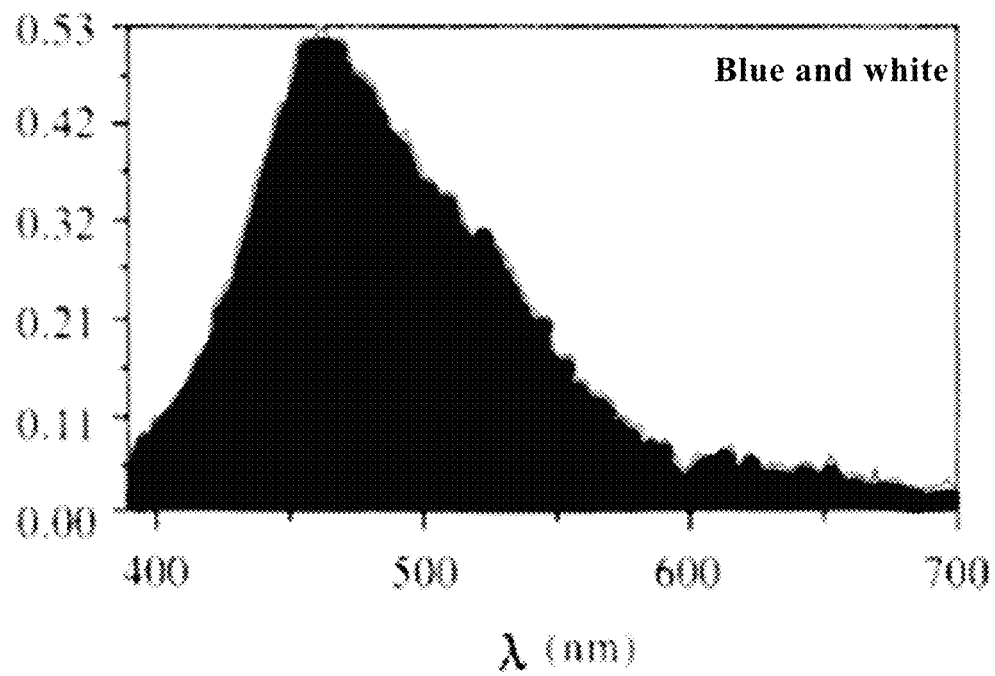
FIG. 2A is a characteristic curve of inherent fluorescence spectrum of normal tissue.

FIG. 2A is a characteristic curve of inherent fluorescence spectrum of normal tissue, and the color of inherent fluorescence spectrum is blue and white.

Figure 2B:
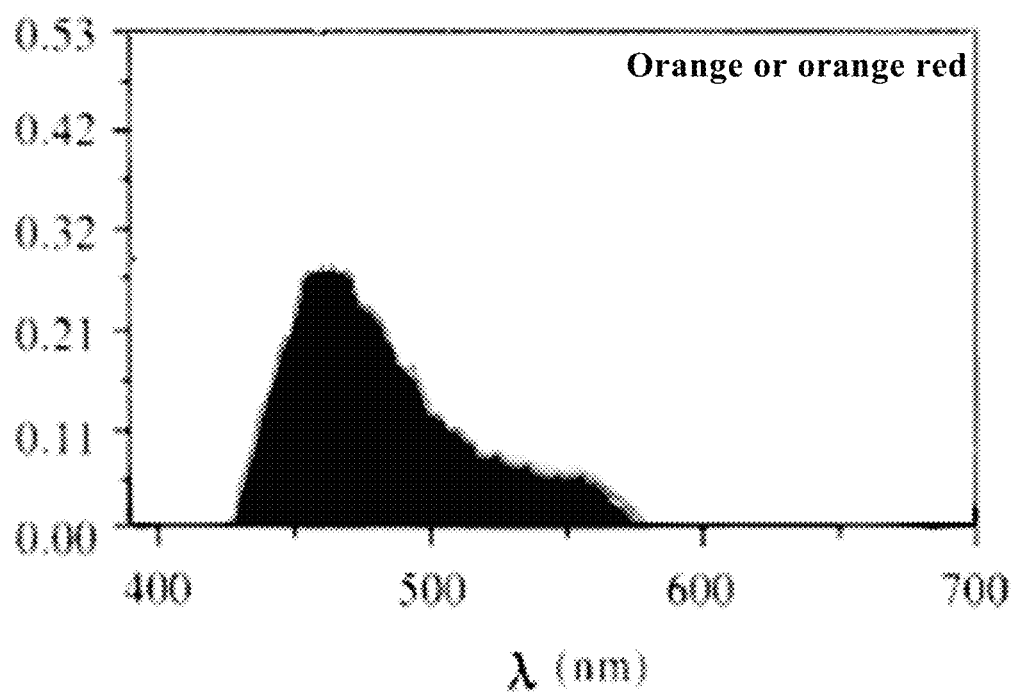
FIG. 2B is a characteristic curve of inherent fluorescence spectrum of benign lesion tissue.

FIG. 2B is a characteristic curve of inherent fluorescence spectrum of benign lesion tissue, and the color of inherent fluorescence spectrum is orange or orange red.

Figure 2C:
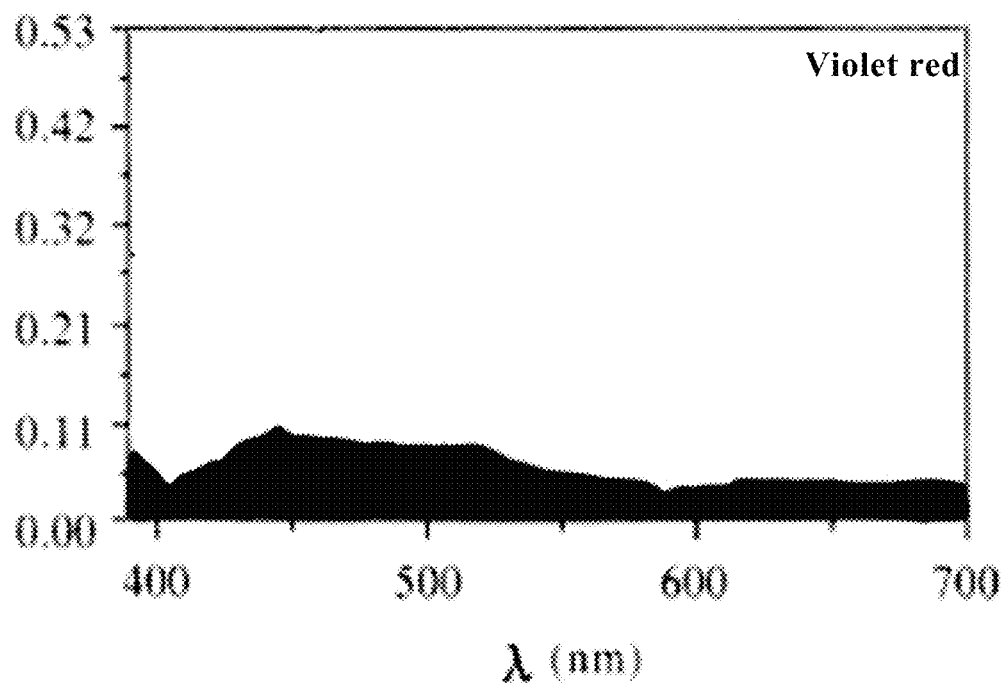
FIG. 2C is a characteristic curve of inherent fluorescence spectrum of cancer tissue.

FIG. 2C is a characteristic curve of inherent fluorescence spectrum of cancer tissue, and the color of inherent fluorescence spectrum is violet red.

Figure 2D:
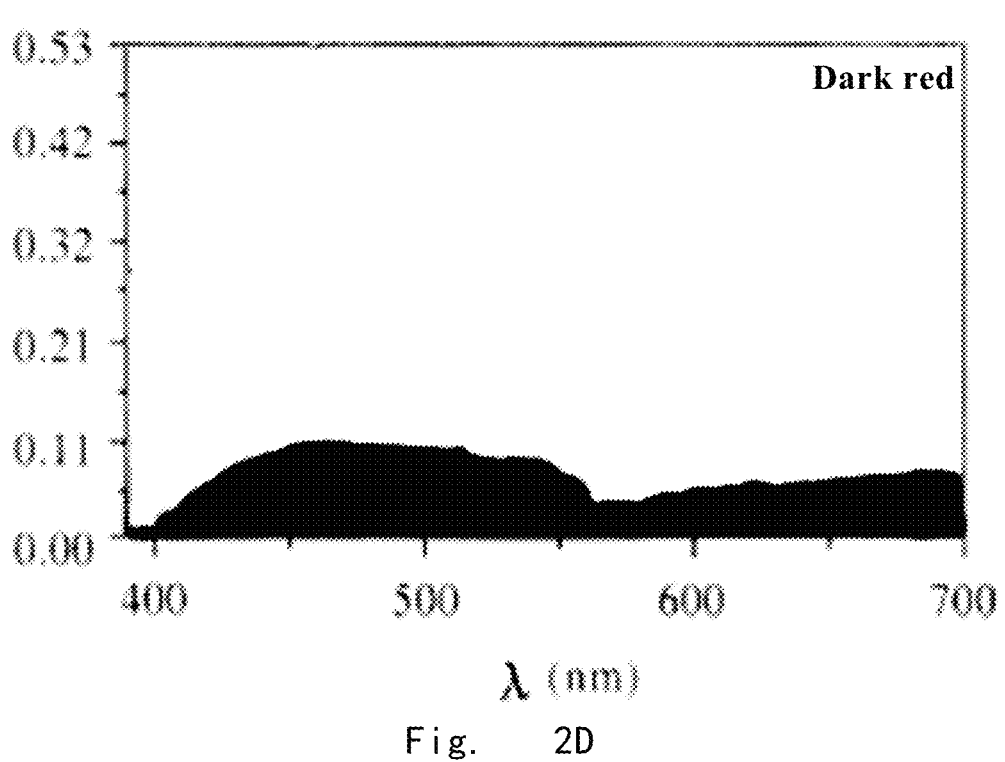
FIG. 2D is a characteristic curve of inherent fluorescence spectrum of severe atypical hyperplasia tissue.

FIG. 2D is a characteristic curve of inherent fluorescence spectrum of severe atypical hyperplasia tissue, the color of inherent fluorescence spectrum is dark red, and there is a possibility of canceration for the severe atypical hyperplasia tissue.

Figure 2E:
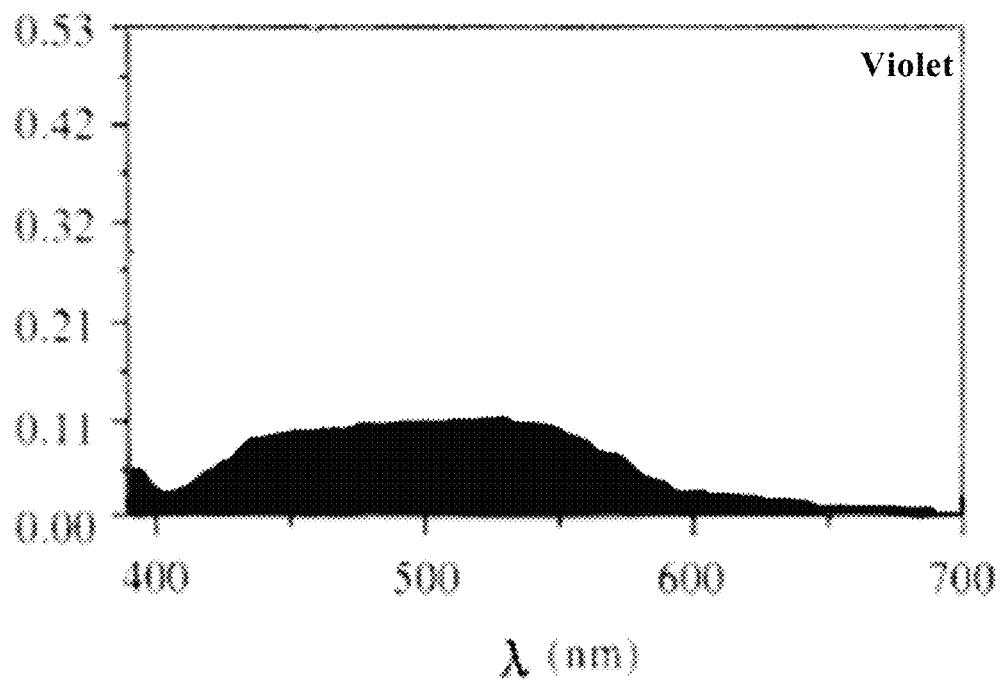
FIG. 2E is a characteristic curve of inherent fluorescence spectrum of severe atypical hyperplasia tissue.

FIG. 2E is a characteristic curve of inherent fluorescence spectrum of severe atypical hyperplasia tissue, the color of inherent fluorescence spectrum is violet, and there is a possibility of canceration for the severe atypical hyperplasia tissue.

Figure 2F:
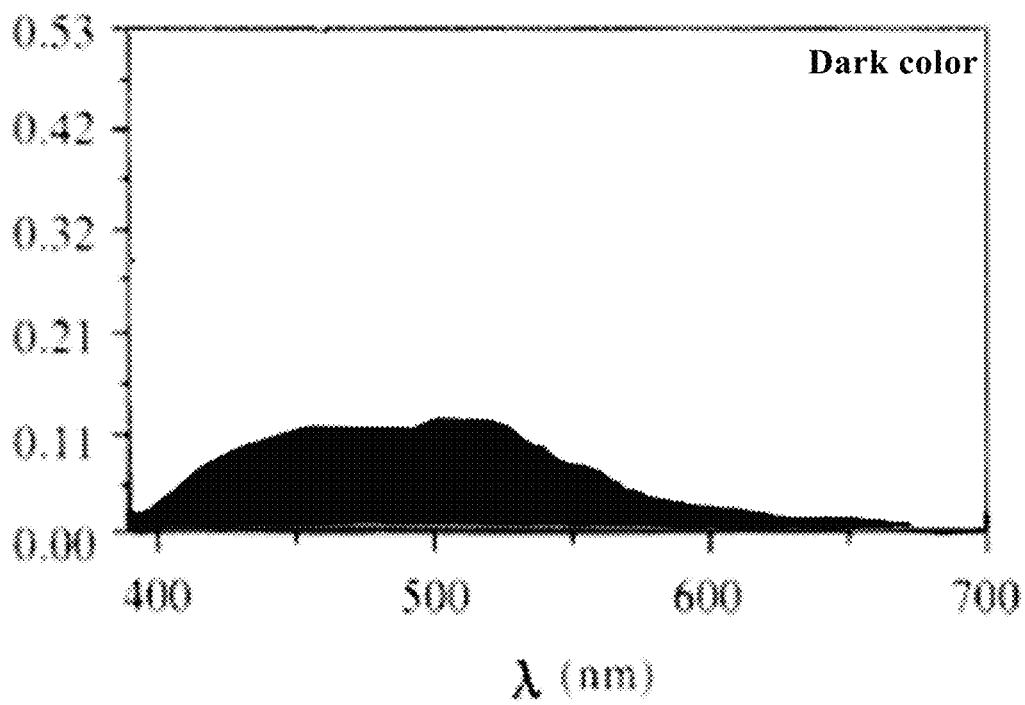
FIG. 2F is a characteristic curve of inherent fluorescence spectrum of mild or moderate atypical hyperplasia tissue.

FIG. 2F is a characteristic curve of inherent fluorescence spectrum of mild or moderate atypical hyperplasia tissue, the color of inherent fluorescence spectrum is dark color, and there temporarily is no possibility of canceration for the mild or moderate atypical hyperplasia tissue.

These curves of inherent fluorescence spectrum and color images of inherent fluorescence truly reflect the biochemistry environment surrounding human tissues. In human tissue, known biological molecules, fluorescence spectrum of which can be detected, comprise amino acid ossein, structure protease and coenzyme, fat and coenzyme related to the cellular metabolic of porphyrin, adenine dinucleotide, flavin adenine dinucleotide (NADH) and flavin mononucleotide, tryptophan, collagen, adermin, elastin, fat intestinal pigment, acriflavine, porphyrin and so on. These molecules will emit respective inherent fluorescence spectrum after being excited by special light, thereby exhibiting their characteristics.

More than 1000 cases of ex vivo specimens removed by surgery have been studied, including specimens of gastric cancer, gastric ulcer, colon adenocarcinoma, endometrial carcinoma. The preferred excitation wavelength and the function relationship of energy and emitted light (EEMexcitation-emission matrices) are studied, i.e., the most effective excitation wavelength and energy conforming to human tissue for exciting the inherent fluorescence are explored. According to the theoretical analysis, longer wavelength and lower energy should be selected to ensure sufficient strength of effective intrinsic fluorescence of human tissue, since short wavelength and high energy are prone to damage the living human tissue and make it photolysis, i.e., "bleached". The requirement on the energy of excitation light reaching tissue is based on real-time detection of thickness of epithelial tissue, and is determined as not more than 0.3~0.5 mj/m². Through extensive testing and analysis, the following conclusions are obtained:

1) Wavelength of Exciting Light

The light-emitting properties of exciting light on the complex of protoporphyrin (protoprphynins Ix bisodium, PP) and bovine serum albumin (Bovinsserdium albu-min, BSA) were studied in a tube. Wavelengths of exciting light were selected as follows: 337 nm, 365 nm, 405 nm. Upon analysis, it is found that the intrinsic fluorescence spectra generated by exciting lights at 337 nm, 365 nm on human tissues are similar, and the peak value of 420 nm is obviously missed in the intrinsic fluorescence spectrum curve generated by exciting light at 405 nm. In Table 1, the fluorescence spectral properties of PP, PP-BSA and tumor tissues under different wavelengths of exciting light are shown.

TABLE 1

| Subject | wavelengths of exciting light λ (nm) | Peak value of fluorescence spectrum |
|---------|---------------------------------------|--------------------------------------|
| PP | 337 | 617, 675 |
| PP-BSA | 337 | 422, 635, 675 |
| Cancer tissue | 337 | 420, 640, 680 |
| PP | 365 | 613, 682 |
| PP-BSA | 365 | 430, 635, 690 |
| Cancer tissue | 365 | 640, 690 |
| PP | 405 | 624, 680 |
| PP-BSA | 405 | 630, 680 |
| Cancer tissue | 405 | 630, 690 |

For the fluorescence spectral properties, the more the positions of characteristics peak value, the more accurate the testing result. 337 nm and 365 nm are much better than 405 nm according to the number of positions of peak values. Therefore, the optimal wavelength of exciting light used in human tissue to excite inherent fluorescence is 340 nm±20 nm.

2) Working Mode of Exciting Light

Pulse mode is better than continuous light. For example, the nitrogen molecule laser belongs to exciting light of pulse mode. Its average power is not high, however its pulse power is very high, which is helpful for the exciting light to enter the inner layer of epithelial tissue through the outer layer of epithelial tissue and explore the biochemical changes in the inner layer of epithelial tissue. In an experiment, it was demonstrated that the exciting light of pulse mode can enter the inner layer of epithelial tissue and discover the characteristic information at 3 mm under the surface of normal mucosa. However, continuous light can not penetrate the epithelial tissue, and the efficient energy of continuous light stays in the outer layer of epithelial tissue, therefore only the inherent fluorescence information of outer layer of epithelial tissue can be detected. Therefore its detectability is not as good as exciting light of pulse mode.

3) Emission Intensity of Exciting Light

The emission intensity of exciting light have basically been determined within a certain range after the wavelength of exciting light was determined at 340 nm±20 nm and the requirement on energy reaching tissue was not higher than 0.3~0.5 mj/m². The human epithelial tissue varies between individuals, but the overall scope of the emission intensity of exciting light is 0.2 Lux~0.6 Lux. In terms of visual inspection, this intensity belongs to lower intensity, which may cause some difficulties in detection. Therefore, the present invention makes a certain design in dealing with the exciting light of weaker intensity, which will be described in detail later.

4) Basic Principles of Identifying Malignant Tumor, Benign Lesion, Atypical Hyperplasia and Normal Tissue According to the Method of Inherent Fluorescence Image:

The diagnosis principle of inherent fluorescence image method is derived from inherent fluorescence spectrum method. The spectrum method can record all the detailed fluorescence informations of the tested tissues, so curves of inherent fluorescence spectrum from more than ten thousand cases of different human tissues (including oral cavity, esophagus, stomach, duodenum, colon, anus and rectum, cervix, uterus, vagina, vulva, nasopharynx, bronchus, skin, and so on) are detected during the period of experiment and data collection, which includes normal tissue, benign lesion, malignant tumor and atypical hyperplasia. According to verification by pathological section and pathological section reports, diagnosis criteria of inherent fluorescence spectrum method were continuously revised, and following diagnosis principles were ultimately determined:

combining the above mentioned characteristic curves of inherent fluorescence spectrum showed in FIG. 2A to FIG. 2F, among the characteristic curves of inherent fluorescence spectrum of various tissues, the following positions of three wavelengths can be used as characteristic point for identifying:

a) 460 nm±20 nm, the above peak value will inevitably appear in all of the tested tissues, and the peak value at this position of wavelength is used as differential diagnosis;

b) 400 nm±20 nm, different tested tissues behave differently, some have this peak value while some not, and the peak value at this position of wavelength is used as differential diagnosis;

c) 670 nm±20 nm, different tested tissues behave differently, some have this peak value while some not, and the peak value at this position of wavelength is used as differential diagnosis.

Self-comparison method was used when making detection and diagnosis. Firstly, the site of normal tissue, i.e., the normal tissue far away from the site suspected as lesion was detected. First of all, the tissue was irradiated with the exciting light at above wavelength and intensity, and the peak values appeared at 460 nm±20 nm in the characteristic curve of detected inherent fluorescence spectrum were determined as 100%. From the comparison of above FIG. 2A to FIG. 2F, it can be seen that there is only a peak value at 460 nm±20 nm for normal tissue. And for other various of lesions (including benign lesions and malignant lesions at each stage), there were several peak values and the peak values at 460 nm±20 nm decrease significantly.

Then the suspicious tissue was detected:

if in the spectrum curve, the peak value at 460 nm±20 nm is less than 50% of that in normal tissue, it is malignant tumor tissue (possibly in different lesion stages), and if more than 50%, it is benign lesion tissue (FIG. 2B);

if in the spectrum curve, there is a peak value at 400 nm±20 nm, the tissue is identified as malignant tumor tissue or atypical hyperplasia tissue;

if in the spectrum curve, there is a peak value at 670 nm±20 nm, the tissue is identified as malignant tumor tissue or atypical hyperplasia tissue too.

The fluorescence spectrum band of inherent fluorescence spectrum method was designed and recorded at 400 nm~700 nm, and the whole band is visible band. The biochemical reaction of epithelial tissue generated by excitation of exciting light at wavelength of 340 nm±20 nm on epithelial tissue can be recorded. The molecular structure can be explored by the characteristic curve of this inherent fluorescence spectrum. Of course, the curve profile of inherent fluorescence spectrum can also be regarded as energy profile of inherent fluorescence spectrum. Since the whole spectrum band of 400 nm~700 nm is distributed in visible band, the intensity of peak also represents the intensity of color. The peak values of different wavelengths can exhibit different colors since the inherent fluorescence imaging method is implemented in visible band. Doctors can directly identify the nature of lesion according to the fluorescent color of lesion through visual method. Referring to FIG. 2A~FIG. 2F again.

As shown in FIG. 2A, the property of energy of inherent fluorescence spectrum of normal epithelial tissue is that: there is a main peak with strong energy at 470 nm (blue) and sub-peaks at 500 nm~600 nm (yellow, orange) and 400 nm~450 nm (blue, purple). The whole visual color is "blue and white".

As shown in FIG. 2B, the property of energy of inherent fluorescence spectrum of benign lesion is that: there is a main peak at 470 nm (blue), which is less than the peak value of normal epithelial tissue at 470 nm, and obvious sub-peaks at 480 nm~580 nm. The whole visual color is "orange or orange red".

As shown in FIG. 2C, the property of energy of inherent fluorescence spectrum of malignant tumor tissue is that: there is a main peak at 470 nm (blue) with greatly reduced energy, some energy i at 500 nm~700 nm and there are sub-peaks at 680 nm (red) and 420 nm. The whole visual color is "violet red".

As shown in FIG. 2D, the property of energy of inherent fluorescence spectrum of severe atypical hyperplasia-malignant tumor lesion is that: there is a main peak at 470 nm (blue) with greatly reduced energy, some energy is still retained at 500 nm~700 nm, and there are sub-peaks at 680 nm (red), but there is no sub-peak at 420 nm. The whole visual color is "dark red".

As shown in FIG. 2E, it is also severe atypical hyperplasia-malignant tumor lesion, which is in different stages of progress comparing with the severe atypical hyperplasia-malignant tumor lesion showed in FIG. 2D. And the property of energy of inherent fluorescence spectrum is that: there is a main peak at 470 nm (blue) with greatly reduced energy, some energy is still retained at 500 nm~700 nm, and there are sub-peaks at 420 nm, but there is no sub-peak at 680 nm (red). The whole visual color is "violet".

As shown in FIG. 2F, the property of energy of inherent fluorescence spectrum of mild or moderate atypical hyperplasia lesion is that: there is a main peak at 470 nm (blue) with greatly reduced energy, and there is no sub-peak at 680 nm (red) and 420 nm. The whole visual color is "dark color".

Based on the above mentioned spectrums, the more precise diagnostic criteria of inherent fluorescence spectrum are showed in Table 2: wherein the energy of peak values near three wavelengths: 460 nm±20 nm, 400 nm±20 nm, 670 nm±20 nm are used as main reference.

TABLE 2

|  | Energy at 460 nm ± 20 nm | Energy at 400 nm ± 20 nm | Energy at 670 nm ± 20 nm | fluorescent color of detected tissue |
| --- | --- | --- | --- | --- |
| Normal tissue | 100% | No | No | blue and white |
| benign lesion tissue | >60% | No | No | orange or orange red |
| malignant tumor tttissue | <40% | Yes | Yes | violet red |
| severe atypical hyperplasia –> cancer | <40% | Yes | None | violet |
| severe atypical hyperplasia –> cancer | <40% | No | Yes | dark red |
| mild or moderate atypical hyperplasia | <40% | No | No | dark color |

Any above lesions are inevitably derived within epithelium, that is, any above lesions are inevitably parasitic in normal epithelial tissue. There is a main peak of strong energy at 470 nm of the fluorescence inherent spectrum of normal epithelial tissue, and its visual color is bright "blue and white". However, the peak value at 470 nm in the inherent fluorescence spectrum of any above lesions, no matter benign lesion, malignant tumor or atypical hyperplasia, is significantly weakened. Therefore, its visual intensity is much less than "blue and white", at least less than 50%~70%. Exciting light sweeps each tissues when taking a quick examination. Each lesion in epithelial tissue will be very obvious against the blue and white background of normal tissues, since the contrast between orange or orange red, violet red, dark red, violet, or dark color and "blue and white" is very significant, and doctors are very easy to visually detect lesion areas. If only a lesion area is to be detected without accurately determining what the lesion is, the presence of a lesion can be preliminarily determined directly according to the color without using self-comparison method.

Optical Observation Equipment

As mentioned above, it is required that the energy reaching tissues is not higher than 0.3~0.5 mj/m$^2$, so the emission intensity of exciting light can be also basically determined within a certain range. The human epithelial tissue varies between individuals, but the overall scope of the emission intensity of exciting light is 0.2 Lux~0.6 Lux. In terms of visual inspection, 0.2 Lux~0.6 Lux is a lower intensity, but it can be visually identified. In specific applications, an equipment, such as endoscope, is needed, since detection and observation need to be performed deeply in human body. When using equipment such as endoscopy, the observed image is actually the image obtained by imaging equipment rather than direct observation of the human eye. For most of the imaging equipments, such as camera, the intensity of 0.2 Lux~0.6 Lux is too low, therefore, the imaging equipments are unable to capture and display the fluorescences. On the other hand, even if such fluorescences can be captured by imaging equipments such as CDD, the signal will be reduced during the process of transmitting the electric signal acquired by CDD to the outside imaging equipment through transmission line of 4 meters, since the endoscope have to be deeply extended into human body, and the length of the endoscope may reach 4 meters. For the fluorescence with an intensity of 0.2 Lux~0.6 Lux, its electric signal is also weak. The attenuation during the transmission process will cause serious distortion to signals and led to deviation of imaging or even no imaging. Taking the requirements on light intensity of imaging equipments in practical application into consideration, the present invention provides an optical observation equipment.

Figure 3:
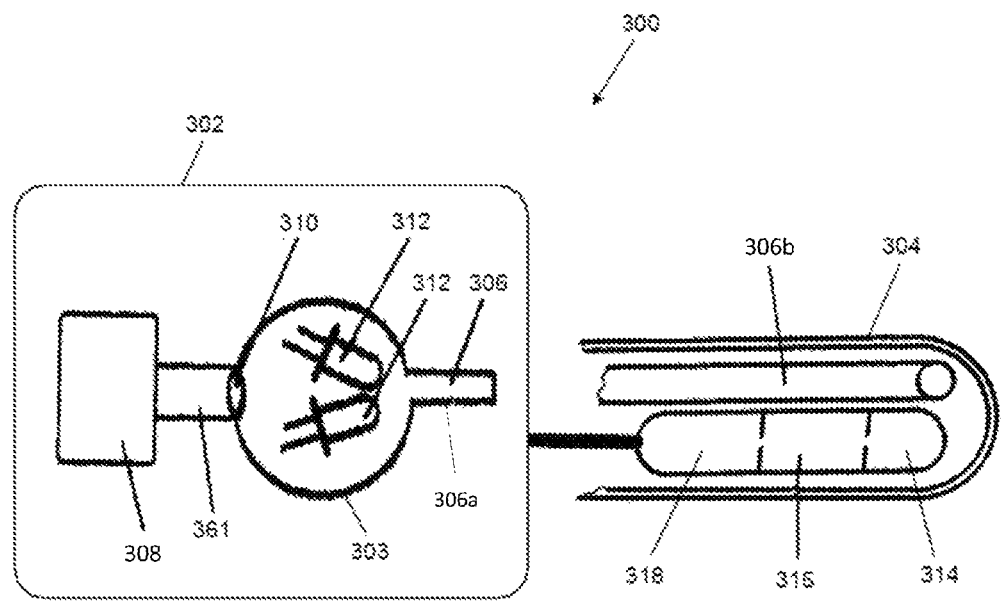
FIG. 3 shows a schematic diagram of the structure of the optical observation equipment according to one embodiment of the present invention.

As shown in FIG. 3, the present invention provides an optical observation equipment for identifying the forming process of a malignant tumor, and the optical observation equipment 300 is provided with a receiving space 302 and a transparent front end 304. The optical observation equipment 300 comprises: a light-guide fiber 306, a laser emitter 308, a focusing device 310, a white light emitter 312, an image sensor 314, a high-gain amplifier 316 and an encoding and emitting device 318.

The light-guide fiber 306 includes an input end 306a and an output end 306b. The input end 306a of light-guide fiber 306 extends to the receiving space 302, and the output end 306b of light-guide fiber 306 extends to the transparent front end 304. The light-guide fiber 306 transmits the laser light with a wave band of 340 nm±20 nm and the white light (solar spectrum), and therefore, the light-guide fiber 306 should possess a low decay rate in these wave bands. In one embodiment, the light-guide fiber 306 is a quartz light-guide fiber or a liquid light-guide fiber which is suitable for the transmission of the ultraviolet band and visible band. In one embodiment, the light-guide fiber shows a low decay rate in the wave band in a range from 300 nm to 700 nm.

The laser emitter 308 is disposed in the receiving space 302 and emits laser with a wavelength of 340 nm±20 nm and an energy of 0.3~0.5 mj/m$^2$ in a pulsing mode. In one embodiment, the laser emitter 308 has a rated output energy >10 mj, a output pulse width <5 ns, a single pulse power >100 KW, and a repeat frequency of 1~50 times/s.

The focusing device 310 is disposed in the receiving space 302 and coupled to the output end of the laser light emitter 308, and the focusing device 310 focuses the laser light emitted by the laser light emitter 308 to the input end 306a of the light-guide fiber 306. In the embodiment shown in FIG. 3, a container 303 is disposed in the receiving space 302, and the container 303 is used for accommodating the white light emitter 312. The output end of laser light emitter 308 is firstly coupled to an input end of a light-guide fiber 361. In one embodiment, the material of light-guide fiber 361 is identical with that of light-guide fiber 306. In one embodiment, the light-guide fiber 361 may only show a low decay rate to the laser light with a wave band of 340 nm±20 nm. An output end of the light-guide fiber 361 is connected to the container 303, and the focusing device 310 (a focusing mirror) is disposed on the output end of light-guide fiber 361. The focusing direction of the focusing device 310 is aligned with on the input end 306a of the light-guide fiber 306. The focusing device 310 focuses the laser light emitted by the laser light emitter 308 to the light-guide fiber 306.

The white light emitter 312 is disposed in the receiving space 302. In the embodiment shown in figures, the white light emitter 312 is disposed in the container 303. The white light emitter 312 is one or several LED (s), and the LED is aligned with the input end of the light-guide fiber 306. The spectrum of LED is a solar spectrum with a color temperature of 5000K±400K. In the embodiment shown in figures, two LEDs (the white light emitter 312) are disposed in the container 303 with a certain angle, and the angle make the LEDs align with the input end of the light-guide fiber 306. The white light emitter 312 emits white light (or sunlight), and the white light is imported into the input end of light-guide fiber 306. In actual use, the laser emitter 308 and the white light emitter 312 are alternately turned on. The white light emitted by white light emitter is used for preliminary observation and screening. The laser emitted by laser emitter is used for exciting fluorescence for identification. The white light emitter should be turned off when a laser is used to excite fluorescence for not affecting the observation of fluorescence, since the intensity of excited fluorescence is relatively low and the intensity of white light is relatively high.

Image sensor 314 is disposed in the transparent front end 304. The image sensor 314 is used for acquiring the image of the area irradiated by light emitted from the output end of the light-guide fiber 306. The image sensor 314 converts light signal into electric signal. In one embodiment, the intensity of excited fluorescence is relatively low, at 0.2 lux~0.6 lux, so a graphene photosensitive element is used in the image sensor 314, which can perceive the fluorescence with an intensity of 0.2 lux~0.6 lux.

The high-gain amplifier 316 is coupled to the image sensor 314 and it is used for amplifying the electric signal generated by the image sensor 314.

The encoding and emitting device 318 is coupled to the high-gain amplifier 316 and it is used for encoding the output from the high-gain amplifier 316 and emitting the encoded signal. In the embodiment, the image sensor 314, the high-gain amplifier 316 and the encoding and emitting device 318 are disposed together and all of them are located in the transparent front end 304, so that the losses during signal transmission between the image sensor 314, the high-gain amplifier 316 and the encoding and emitting device 318 can be reduced or even avoided. The signal acquired by image sensor 314 is amplified and encoded, and then emitted in an encoded mode. According to the prior art, the transmission of encoded image signal can reach a far distance no matter by the way of wire transmission or wireless transmission, the loss during the process of transmission is very small, and the signal can be restored to clear image at the receiving end. An important characteristic of the optical observation equipment of present invention is that the acquired image is firstly encoded, and then transmitted as an encoded signal, so that the back-end coding method that commonly employed in the prior art can be changed, and the losses of electric signal generated by the image sensor during transmission process can be avoided. It should be noted that the image sensor 314, the high-gain amplifier 316 and the encoding and emitting device 318 are commercially available equipments, which can be purchased from the market according to specific parameter requirements. Only the parameters are emphasized herein.

The encoded signal emitted by the encoding and emitting device 318 is received by a receiving and decoding device (not shown in the figure). The encoded signal is decoded by the receiving and decoding device and then provided to a image processing device (not shown in the figure). The image processing device restores the image acquired by the image sensor and displays the image. The coding and decoding of image signal can be achieved using the existing image processing and transmission technology, which is not necessary to be described herein.

Endoscope

Figure 4:
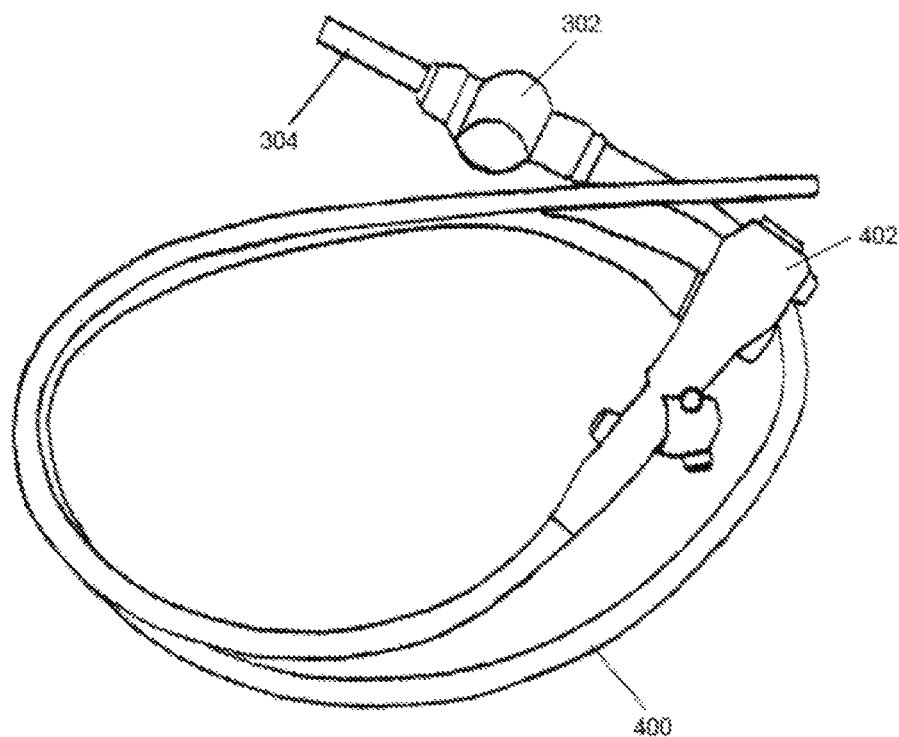
FIG. 4 shows a schematic diagram of the structure of the endoscope according to one embodiment of the present invention.
Figure 5:
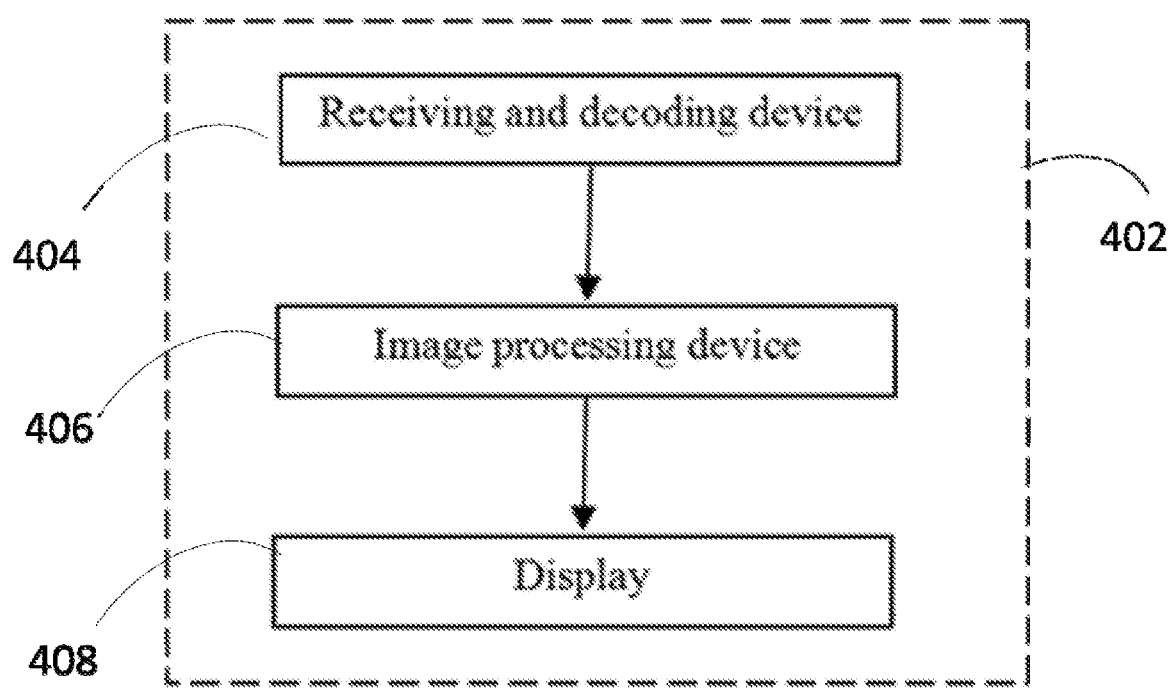
FIG. 5 shows a schematic diagram of the structure of an image processing terminal according to an embodiment of the present invention.

FIG. 4 shows a schematic diagram of the structure of endoscope in one embodiment of the present invention. As shown in FIG. 4, the present invention also provides an endoscope for identifying the forming process of a malignant tumor. The optical observation equipment 300 is disposed in the front end of the endscope 400. Moreover, the receiving space 302 and the transparent front end 304 are formed in endoscope 400. The endoscope 400 further includes an image processing terminal 402. In the embodiment shown in figures, the image processing terminal 402 is formed on the back end of the endoscope. Referring to FIG. 5, the image processing terminal 402 includes a receiving and decoding device 404, an image processing device 406, and a display 408. The encoded signal emitted by the encoding and emitting device 318, which is shown in FIG. 3, is received and decoded by the receiving and decoding device 404, and then provided to an image processing device 406, which restores the image acquired by the image sensor and displays the image on the display 408. The process of coding, transmission, decoding and restoration of the image can be achieved by existing technology, which is not described here. When the image processing terminal 402 is integrated on the back end of the endoscope, a wired mode can be used for the signal transmission between the encoding and emitting device 318 and the receiving and decoding device 404, such as transmission by cable or optical fiber.

In other embodiments, the image processing terminal 402 can also be separated from the main body of endoscope. The image processing terminal can be a separate device. The advantage of this setting is that a larger display can be installed. If separate setting is employed, a wireless mode can be used in the signal transmission between "encoding and emitting device" and "receiving and decoding device".

Alternatively, two image processing terminals can be set, that is, an image processing terminal is installed on the back end of the endoscope and a smaller display is equipped for the direct observation of the operating doctor. And another image processing terminal is installed in a separate position and a bigger display is equipped for the observation of other doctor.

Identification Method

The present invention also provides an method for identifying the forming process of a malignant tumor by using the above mentioned endoscope, the method comprising:

calibrating the laser emitter, wherein the output energy and output frequency of exciting light should be firstly calibrated to ensure clinical application, and the energy of laser reaching the tissue to be tested should be within 0.3~0.5 mj/m$^2$ in the clinical application. The calibration step of laser emitter comprises turning on the laser emitter, adjusting the laser emitter to a state of mono-pulse output, inserting a laser energy meter to detect the output energy of the laser emitter, calibrating the output energy to 2 mj/s and setting the working frequency to 50 times/s.

Stretching the endoscope into a human body, and letting the front end of endoscope reach the area of tissue to be detected.

Turning off the laser emitter, turning on the white light emitter, and irradiating the tissue to be detected with a white light emitted from the output end of the light-guide fiber.

Displaying the image of the tissue to be detected which is irradiated by the white light in a display via the image sensor, the high-gain amplifier, the encoding and emitting device, the receiving and decoding device and the image processing device, and identifying suspected tissue area. Under the irradiation of white light, the general morphologic changes of tissues are observed through the display of image processing terminal. The preliminary judgment of tissues is still performed based on morphology in this step. And the suspected tissue area that is suspected of the existence of lesions is identified.

Turning off the white light emitter, turning on the laser emitter, and irradiating the suspected tissue area with a laser emitted from the output end of the light-guide fiber in a pulse mode.

Displaying the fluorescence image of the suspected tissue area which is irradiated by the laser in the display via the image sensor, the high-gain amplifier, the encoding and emitting device, the receiving and decoding device and the image processing device.

Identifying whether or not the suspected area is relevant to malignant tumor according to the fluorescence color, wherein the peak value of energy at 460 nm±20 nm of normal tissue is used as a reference, if the peak value at 460 nm±20 nm is 100% of the reference value, there is no other peak values, and the fluorescence color is blue and white, the tissue is identified as normal tissue;

if the peak value at 460 nm±20 nm is more than 60% of the reference value, there is no other peak values, and the fluorescence color is orange or orange red, the tissue is identified as benign lesion tissue;

if the peak value at 460 nm±20 nm is less than 40% of the reference value, there are peak values at 400 nm±20 nm and 670 nm±20 nm, and the fluorescence color is violet red, the tissue is identified as malignant tumor tissue;

if the peak value at 460 nm±20 nm is less than 40% of the reference value, there is peak value at 400 nm±20 nm, and the fluorescence color is violet, the tissue is identified as severe atypical hyperplasia tissue;

if the peak value at 460 nm±20 nm is less than 40% of the reference value, there is peak value at 670 nm±20 nm, and the fluorescence color is dark red, the tissue is identified as severe atypical hyperplasia tissue;

if the peak value at 460 nm±20 nm is less than 40% of the reference value, there is no other peak values, and the fluorescence color is dark color, the tissue is identified as mild or moderate atypical hyperplasia tissue.

When irradiating the suspected tissue area with the laser emitter, the scope of irradiation can be properly enlarged to avoid the shortcomings in the existing morphology-based identification method. That is, the area surrounding suspected tissue is also irradiated with a laser. Those areas is probably in a state of precancerous lesion, which may be easily identified as normal tissues by traditional morphological judgment, while can be judged whether or not it belongs to atypical hyperplasia based on fluorescence spectrum through laser irradiation.

For the tissues identified as malignant tumor, severe atypical hyperplasia and mild or moderate atypical hyperplasia through fluorescence spectrum, physiology section should be taken for more accurate pathological diagnosis.

The present invention also provides an method for identifying the forming process of a malignant tumor using the above mentioned optical observation equipment rather than endoscope. The application field of this optical observation equipment is broader than that of the endoscope. For some tissues, such as oral cavity, cervix, anus and rectum which can be easily and directly observed, the optical observation equipment can be directly used for irradiation. Alternatively, the optical observation equipment can be used to directly irradiate and observe tissues which can be directly observed during the process of a surgical operation. As mentioned above, in terms of visual inspection, 0.2 Lux~0.6 Lux is a lower intensity, however it can be visually identified. Therefore, the fluorescence can be directly observed by visual inspection without using imaging equipment in the place of direct observation.

The method comprises:

aligning the transparent front end of the optical observation equipment with a tissue to be detected.

Turning off the laser emitter, turning on the white light emitter, and irradiating the tissue to be detected using the white light emitted from the output end of the light-guide fiber.

Displaying the image of the tissue to be detected which is irradiated by the white light in a display via the image sensor, the high-gain amplifier, the encoding and emitting device, the receiving and decoding device and the image processing device, and identifying suspected tissue area. It can also suitably be directly observed by visual inspection, without using the image sensor, the high-gain amplifier, the encoding and emitting device, the receiving and decoding device and the image processing device.

Turning off the white light emitter, turning on the laser emitter, and irradiating the suspected tissue area using the laser emitted from the output end of the light-guide fiber in a pulse mode.

Displaying the fluorescence image of the suspected tissue area which is irradiated by the laser in the display via the image sensor, the high-gain amplifier, the encoding and emitting device, the receiving and decoding device and the image processing device. The fluorescence image can also suitably be directly observed by visual inspection, without using the image sensor, the high-gain amplifier, the encoding and emitting device, the receiving and decoding device and the image processing device.

Identifying whether or not the suspected area is relevant to malignant tumor according to the fluorescence color, wherein the peak value of energy at 460 nm±20 nm of normal tissue is used as a reference, if the peak value at 460 nm±20 nm is 100% of the reference value, there is no other peak values, and the fluorescence color is blue and white, the tissue is identified as normal tissue;

if the peak value at 460 nm±20 nm is more than 60% of the reference value, there is no other peak values, and the fluorescence color is orange or orange red, the tissue is identified as benign lesion tissue;

if the peak value at 460 nm±20 nm is less than 40% of the reference value, there are peak values at 400 nm±20 nm and 670 nm±20 nm, and the fluorescence color is violet red, the tissue is identified as malignant tumor tissue;

if the peak value at 460 nm±20 nm is less than 40% of the reference value, there is a peak value at 400 nm±20 nm, and the fluorescence color is violet, the tissue is identified as severe atypical hyperplasia tissue;

if the peak value at 460 nm±20 nm is less than 40% of the reference value, there is a peak value at 670 nm±20 nm, and the fluorescence color is dark red, the tissue is identified as severe atypical hyperplasia tissue;

if the peak value at 460 nm±20 nm is less than 40% of the reference value, there is no other peak values, and the fluorescence color is dark color, the tissue is identified as mild or moderate atypical hyperplasia tissue;

The optical observation equipment, the endoscope using the optical observation equipment and the related identification method of the present invention can identify the tumors in stage of precancerous lesion, especially the malignant tumors with lesions smaller than 5 mm in time, i.e., the malignant tumors in the forming process.

The above mentioned embodiments are provided to the skilled person in the art for realizing or using the present invention. The skilled person can make various modifications or amendments to the above mentioned embodiments without departing from the ideas of the present invention. Therefore, the protection scope of the present invention is not limited by the above mentioned embodiments, while should be the maximum scope conforming with the innovative features referred by the claims.

The invention claimed is:

1. An optical observation equipment for identifying a forming process of a malignant tumor, wherein the optical observation equipment has a receiving space and a transparent front end, and the optical observation equipment comprises:

a light-guide fiber, an input end of which extends to the receiving space and an output end of which extends to the transparent front end;

a laser light emitter disposed in the receiving space, the laser light emitter being capable of emitting a laser light that is guided into the input end of the light-guide fiber, the laser light having a wavelength of 340 nm±20 nm and an energy in a range from 0.3 mj/m$^2$ to 0.5 mj/m$^2$ in a pulsing mode;

a focusing device comprising a focusing mirror that is disposed in the receiving space and coupled to the output end of the laser light emitter, and the focusing device being capable of focusing the laser to the input end of the light-guide fiber;

a white light emitter disposed in the receiving space, the white light emitter being capable of emitting a white light that is guided into the input end of the light-guide fiber, wherein the laser light emitter and the white light emitter are alternately turned on;

an image sensor disposed in the transparent front end, and the image sensor being capable of acquiring an image of an area irradiated by a white light or laser light emitted from the output end of the light-guide fiber and converting a light signal of the image into an electrical signal; and a gain amplifier coupled to the image sensor, the gain amplifier being capable of amplifying the electrical signal generated by the image sensor.

2. The optical observation equipment for identifying the forming process of the malignant tumor of claim 1, wherein the laser light emitter has an output pulse width <5 ns, and a repeat frequency in a range from 1 time/s to 50 times/s.

3. The optical observation equipment for identifying the forming process of the malignant tumor of claim 1, wherein the white light emitter includes one or several light-emitting diodes (LEDs) that are aligned with the input end of the light-guide fiber and have a solar spectrum with a color temperature of 5000K±400K.

4. The optical observation equipment for identifying the forming process of the malignant tumor of claim 1, wherein the light-guide fiber is a quartz light-guide fiber or a liquid light-guide fiber suitable for transmission of ultraviolet band and visible band.

5. The optical observation equipment for identifying the forming process of the malignant tumor of claim 1, wherein the image sensor includes a graphene photosensitive element capable of detecting a fluorescence with an intensity in a range from 0.2 lux to 0.6 lux.

6. A method for identifying a forming process of a malignant tumor, comprising:

aligning the transparent front end of the optical observation equipment of claim 1 with a tissue to be detected;

turning off the laser light emitter, turning on the white light emitter, and irradiating the tissue with a white light emitted from the output end of the light-guide fiber;

acquiring a first image of an area of the tissue irradiated by the white light emitted from the output end of the light-guide fiber and converting the light signal of the first image into a first electrical signal;

amplifying the first electrical signal with the gain amplifier;

encoding and emitting a first signal output of the gain amplifier to obtain a first encoded signal;

receiving and decoding the first encoded signal;

restoring the first image;

displaying the first image on a display, and identifying a suspected area of the tissue;

turning off the white light emitter, turning on the laser light emitter, and irradiating the suspected area with a laser light emitted from the output end of the light-guide fiber in a pulse mode, the laser light having a wavelength of 340 nm±20 nm and an energy in a range from 0.3 mj/m$^2$ to 0.5 mj/m$^2$ in a pulsing mode;

acquiring a fluorescence image of the suspected area irradiated by the laser light emitted from the output end of the light-guide fiber and converting the light signal of the fluorescence image into a second electrical signal with the image sensor;

amplifying the second electrical signal with the gain amplifier;

encoding and emitting a second signal output of the gain amplifier to obtain a second encoded signal;

receiving and decoding the second encoded signal;

restoring the fluorescence image;

displaying the fluorescence image on the display and obtaining a fluorescence spectrum of the tissue;

identifying whether or not the suspected area is relevant to the malignant tumor on the basis of the fluorescence spectrum, wherein a peak value at 460 nm±20 nm of a fluorescence spectrum of normal tissue is used as a reference value, if the fluorescence spectrum of the tissue has a peak value at 460 nm±20 nm that is 100% of the reference value, and the fluorescence spectrum of the tissue has no peak values at 400±20 nm and 670±20 nm, the tissue is identified as a normal tissue;

if the fluorescence spectrum of the tissue has a peak value at 460 nm±20 nm that is more than 60% of the reference value, and the fluorescence spectrum of the tissue has no peak values at 400±20 nm and 670±20 nm of the fluorescence spectrum, the tissue is identified as a benign lesion tissue;

if the fluorescence spectrum of the tissue has a peak value at 460 nm±20 nm that is less than 40% of the reference value, and the fluorescence spectrum of the tissue has peak values at 400 nm±20 nm and 670 nm±20 nm the tissue is identified as the malignant tumor tissue;

if the fluorescence spectrum of the tissue has a peak value at 460 nm±20 nm that is less than 40% of the reference value, the fluorescence spectrum of the tissue has a peak value at 400 nm±20 nm, and the fluorescence spectrum of the tissue has no peak value at 670 nm±20 nm, the tissue is identified as a severe atypical hyperplasia tissue;

if the fluorescence spectrum of the tissue has a peak value at 460 nm±20 nm that is less than 40% of the reference value, the fluorescence spectrum of the tissue has a peak value at 670 nm±20 nm, and the fluorescence spectrum of the tissue has no peak value at 400 nm±20 nm, the tissue is identified as a severe atypical hyperplasia tissue; and if the fluorescence spectrum of the tissue has a peak value at 460 nm±20 nm that is less than 40% of the reference value, and the fluorescence spectrum of the tissue has no peak values at 400 nm±20 nm and 670 nm±20 nm, the tissue is identified as a mild or moderate atypical hyperplasia tissue.

7. An endoscope for identifying a forming process of a malignant tumor, comprising the optical observation equipment according to claim 1 at a front end thereof.

8. The endoscope for identifying the forming process of a malignant tumor according to claim 7, wherein the transparent front end is at one end of the endoscope, and an image processing terminal is at an other end of the endoscope.

* * * * *